United States Patent
Pescatore et al.

(10) Patent No.: US 7,671,887 B2
(45) Date of Patent: Mar. 2, 2010

(54) SYSTEM AND METHOD OF NAVIGATING A MEDICAL INSTRUMENT

(75) Inventors: Jeremie Pescatore, Yvelines (FR); Yves Trousset, Palaiseau (FR); Michel F. Grimaud, Montrouge (FR); Daniel E. Groszmann, Cambridge, MA (US)

(73) Assignee: General Electric Company, Schenectady, NY (US)

( * ) Notice: Subject to any disclaimer, the term of this patent is extended or adjusted under 35 U.S.C. 154(b) by 595 days.

(21) Appl. No.: 11/561,727

(22) Filed: Nov. 20, 2006

(65) Prior Publication Data

US 2008/0118103 A1    May 22, 2008

(51) Int. Cl.
*H04N 5/14*    (2006.01)
(52) U.S. Cl. .................. 348/25; 348/113; 348/116; 348/77; 348/141; 348/142; 348/169; 382/103; 600/424; 600/427
(58) Field of Classification Search ........... 348/25, 348/113, 116, 77, 141, 142, 169; 382/103; 600/424, 427
See application file for complete search history.

(56) References Cited

U.S. PATENT DOCUMENTS

| | | | |
|---|---|---|---|
| 5,636,255 A | 6/1997 | Ellis | |
| 5,822,396 A | 10/1998 | Navab et al. | |
| 6,490,475 B1 | 12/2002 | Seeley et al. | |
| 6,533,455 B2 | 3/2003 | Graumann et al. | |
| 6,738,656 B1 | 5/2004 | Ferre et al. | |
| 6,782,287 B2 * | 8/2004 | Grzeszczuk et al. | 600/424 |
| 2003/0220557 A1 | 11/2003 | Cleary et al. | |
| 2004/0013240 A1 | 1/2004 | Mitschke et al. | |
| 2008/0123910 A1 * | 5/2008 | Zhu | 382/128 |

OTHER PUBLICATIONS

Groszmann, D., Anderson, P., Beauregard, G., Jensen, V., Methods and Systems for Registration of Surgical Navigation Data and Image Data. U.S. Appl. No. 11/371,739, Mar. 9, 2006.

* cited by examiner

*Primary Examiner*—Shawn An (57) ABSTRACT

A system for navigating an image-guided object through an imaged subject supported on table in relation to an image acquired by an image detector is provided. The system includes a first tracking element attached to the patient, and a second tracking element attached at the table. The first and second tracking elements define first and second coordinate systems. A controller is operable to register the second coordinate system with a third coordinate system defined by the image detector, measure a spatial relation between the first tracking element and the second tracking element, register the first coordinate system with the third local coordinate system defined by the image detector based on the spatial relation between the first and second tracking elements, and generating a composite image comprising a virtual image of the object in spatial relation to the image of the imaged subject acquired by the image detector.

20 Claims, 4 Drawing Sheets

SYSTEM AND METHOD OF NAVIGATING A MEDICAL INSTRUMENT

BACKGROUND OF THE INVENTION

The subject matter herein generally relates to a medical diagnostic imaging, and more specifically, to a system and method of navigating an object through an imaged subject.

Image-guided surgery is a developing technology that generally provides a surgeon with a virtual roadmap into a patient's anatomy. This virtual roadmap allows the surgeon to reduce the size of entry or incision into the patient, which can minimize pain and trauma to the patient and result in shorter hospital stays. Examples of image-guided procedures include laparoscopic surgery, thoracoscopic surgery, endoscopic surgery, etc. Conventional medical diagnostic imaging tools such as computerized tomography (CT), magnetic resonance imaging (MRI), positron emission tomography (PET), ultrasound, radiological machines, etc. can be useful in providing static image guiding assistance in such procedures. The above-described imaging tools can provide two-dimensional or three-dimensional images that can be displayed to provide a surgeon or clinician with an illustrative map of an area of interest of a patient's body.

Certain tracking systems have been developed for monitoring the position and movement of a surgical instrument or object relative the above-described images. Generally, as a surgeon moves the medical instrument with respect to the patient's anatomy, virtual images of the instrument or object are displayed relative to the acquired images. These certain conventional tracking systems employ the use of passive articulated mechanical arms, electromagnetic detection, optical detection, and ultrasonic detection to track a location of the instrument with respect to the patient's anatomy. Computer programmed algorithms are then employed to track the spatial relationship between the tracked instrument or object and the acquired image.

Conventional techniques employed to measure or determine the spatial relationship between the tracked object and the acquired images includes placing fiduciary landmarks or structures on the patient. The acquired images illustrate the fiduciary landmarks as opaque spots that define a coordinate system relative to the patient. Such fiduciary landmarks located in the operating space illustrated in the acquired image are used to locate and track movement of the medical instrument through the operating space.

There is a need for a system and method of tracking that more simply and readily tracks the spatial relationship of the medical instruments or objects traveling through an operating space of patient. The system should be simple to manufacture and operate, and need not rely on illustrating fiducial marks, landmarks or structures in the acquired image of the operating space to track movement of the object therethrough.

BRIEF DESCRIPTION OF THE INVENTION

The above-mentioned need is addressed by the embodiments of the subject matter described herein in the following description.

In accordance with one embodiment, a system for navigating an image-guided object traveling in an area of interest of an imaged subject supported on table in relation to an acquired image of the imaged subject is provided. The system includes an image detector operable to generate the acquired image of the imaged subject. The image detector defines a detector coordinate system. The system further includes a gantry in mobile support of the image detector relative to the table. The gantry defines a gantry coordinate system. The system further includes a first tracking element attached at the table in support of the imaged subject, the first tracking element defining a first tracking coordinate system. The first tracking element is not located within a field of view of the image detector. The system further includes a second tracking element attached at the object traveling through the imaged subject, the second tracking element in electromagnetic communication with the first tracking element. The second tracking element defines a second tracking coordinate system. The system further includes a controller electrically connected in communication with the first and second tracking elements. The controller includes a processor operable to execute a plurality of program instructions stored in a memory. The plurality of program instructions comprise registering the image coordinate system with the detector coordinate system; acquiring a spatial relation between the detector coordinate system and the gantry coordinate system; acquiring a spatial relation between the gantry coordinate system and a table coordinate system defined by the table; registering the first tracking coordinate system defined by the first tracking element with respect to the table coordinate system; acquiring the spatial relation between the first tracking element in communication with the second tracking element; translating the spatial relation between first tracking element at the table and the second tracking element at the object automatically into a spatial relation of the object relative to the image; and generating a composite image comprising a virtual image of the object in spatial relation to the image of the imaged subject acquired by the image detector.

An embodiment of a method of navigating an image-guided object through an area of interest of an imaged subject is provided. The method comprises acquiring an image of the imaged subject with an image detector; acquiring a spatial relation between a detector coordinate system defined by a location of the image detector and a gantry coordinate system defined by a location of a gantry in mobile support of the image detector; acquiring a spatial relation between the gantry coordinate system and a table coordinate system defined by a location of the table; registering the table coordinate system with a first tracking element attached at the table, the first tracking element defining a first tracking coordinate system; acquiring a spatial relation between the first tracking element relative to a second tracking element attached at the object; translating the spatial relation between first tracking element at the table and the second tracking element at the object automatically into a spatial relation of the object relative to the image coordinate system; and generating a composite image comprising a virtual image of the object in spatial relation to the image of the imaged subject.

Still also, an embodiment of a system for navigating an image-guided object traveling in an area of interest of an imaged subject supported on a table is provided. The system comprises an image detector operable to acquire an image of the imaged subject, and a gantry in mobile support of the image detector in relation to the table. The system also includes first, second and third tracking elements. The first tracking element is attached at the table and defines a first tracking coordinate system. The first tracking element is not located within a field of view of the image. The second tracking element is attached at the image-guided object traveling through the imaged subject, the second tracking element in communication with the first tracking element. The third tracking element is attached to the imaged subject and in communication with both the first and second tracking elements, the third tracking element defining a third tracking coordinate system. The system further includes a controller electrically connected in communication with the image detector and the first, second, and third tracking elements, the controller having a processor in communication with a memory. The processor is operable to execute a plurality of program instructions stored in the memory, the plurality of program instructions comprising the acts of registering an image coordinate system of the image of the imaged subject with a detector coordinate system defined by a location of the image detector; acquiring a spatial relation between the detector coordinate system and a gantry coordinate system defined by a location of the gantry; acquiring a spatial relation between the gantry coordinate system and a table coordinate system defined by the table; registering the first tracking coordinate system with respect to the table coordinate system; acquiring the spatial relation between the second tracking element and the object navigated through the imaged subject; acquiring the spatial relation between the first tracking element and the second tracking element; translating the spatial relation between first tracking element at the table and the second tracking element at the object automatically into a spatial relation of the object relative to the image of the imaged subject; and generating a composite image comprising a virtual image of the object in spatial relation to the image of the imaged subject acquired by the image detector.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
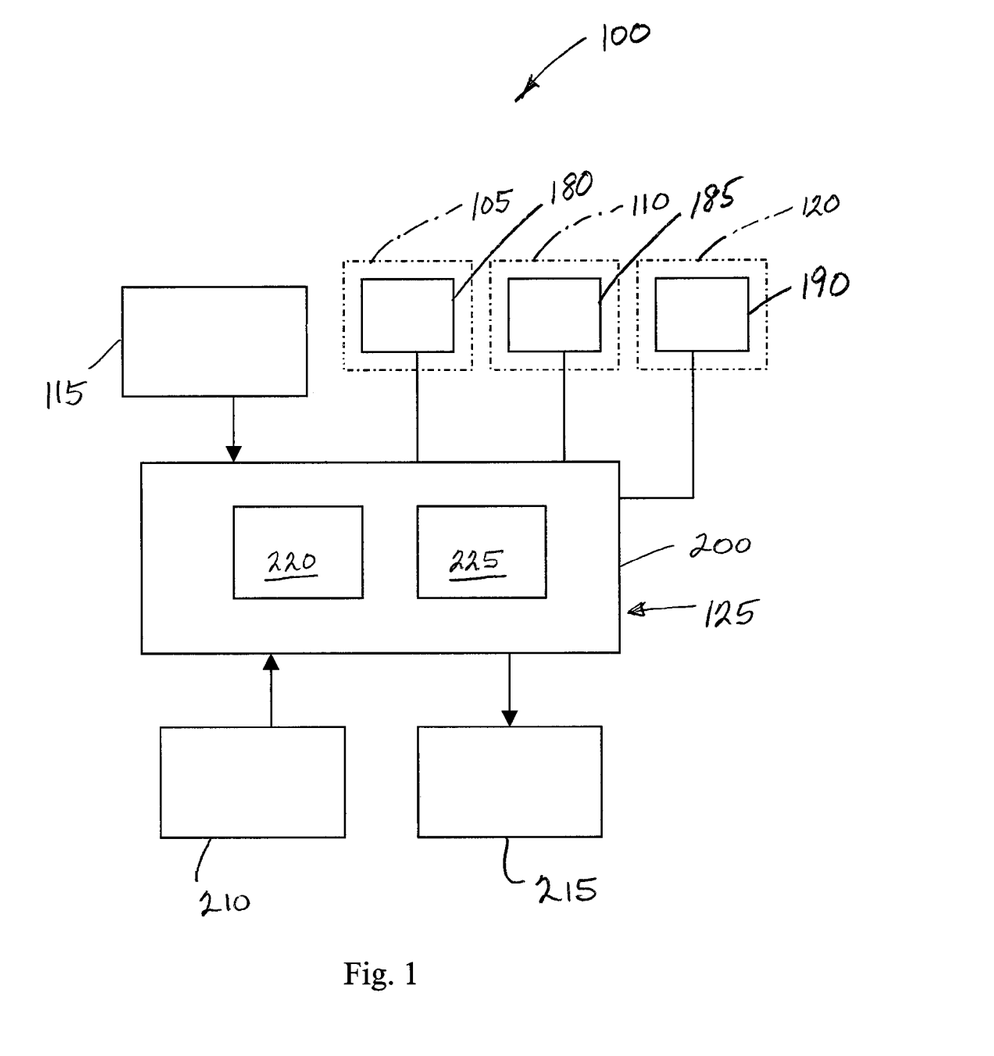
FIG. 1 shows a schematic block diagram illustrative of an embodiment of a system operable to track an object through an anatomy of an imaged subject.

FIG. 1 illustrates an embodiment of a system 100 operable to track movement of a tool or object 105 through an anatomy of an imaged subject 110. The system 100 generally includes an image acquiring system 115, a table 120 in support of the imaged subject 110, and a tracking system 125 operable to track a position of the object 105 traveling through the imaged subject 110.

The image acquiring system 115 is generally operable to generate a two-dimensional, three-dimensional, or four-dimensional image data corresponding to an area of interest of the imaged subject 110. Examples of the image acquiring system 115 can include, but is not limited to, computed tomography (CT), magnetic resonance imaging (MRI), x-ray, positron emission tomography (PET), tomosynthesis, ultrasound, angiographic, fluoroscopic, and the like or combination thereof. The image acquiring system 115 can be operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure. Thus, the types of images can be diagnostic or interventional. In one example, the image acquiring system 115 includes a static image acquiring system in combination with a real-time image acquiring system. In another example, the image acquiring system 115 is configured to generate a fusion of an image acquired by a CT imaging system with an image acquired by an MR imaging system. This embodiment can be employed in the surgical removal of tumors. The tumor is generally visible in the MR image, and the bone structure is generally visible in the CT image. The acquired image data is communicated directly or indirectly from the image acquiring system 115 via a communication link to the tracking system 125.

Figure 2:
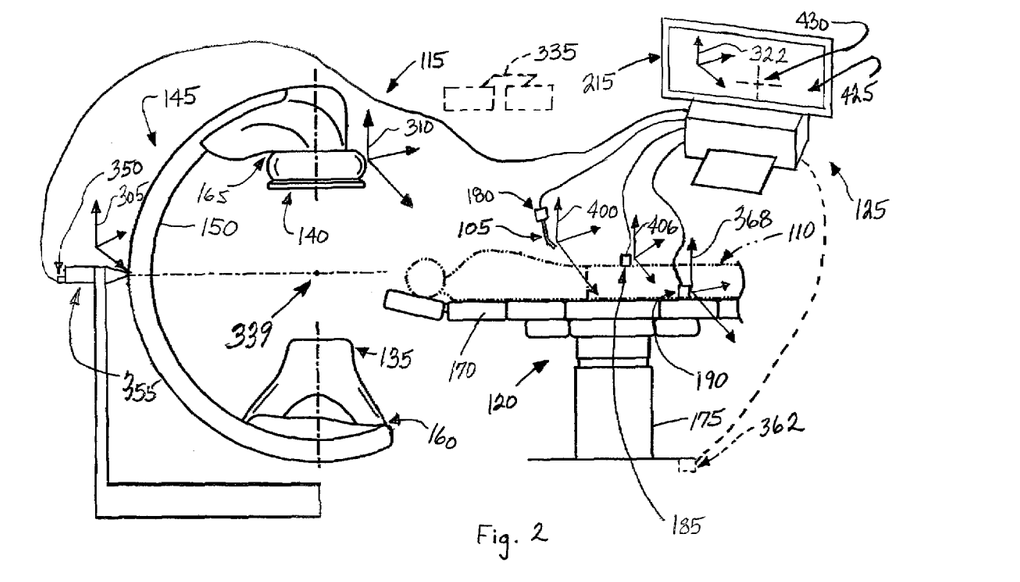
FIG. 2 shows a schematic diagram of an embodiment of the system for tracking an object through an anatomy of an imaged subject.

Referring to FIG. 2, an exemplary image acquiring system 115 is a X-ray imaging system operable to pass X-rays through the imaged subject 110 and then detect and process a diagnostic image for interpretation. The illustrated image acquiring system 115 generally includes a radiation source 135 and a detector or receiver 140. The exemplary radiation source 135 generates an X-ray photons preferably directed to form an X-ray beam. The X-ray beam has an axis 142 that is substantially aligned with the center of the active area of the detector 140.

Still referring to FIG. 2, the image acquiring system 115 further includes a movable support assembly or gantry 145 in mobile support of the radiation source 135 and detector 140 in relation to the imaged subject 110 resting on the table 120. The gantry 145 is mounted with a mobile arm 150. The illustrated mobile arm 150 is a C-arm having a pair of opposed free ends 160 and 165. The radiation source 135 is connected at the first free end 160, and the detector 140 is connected at the second free end 165 in opposed relation to radiation source so as to receive attenuated radiation passing through the imaged subject 110 located therebetween. The mobile arm 150 is generally operable to rotate about several axes so as to position the radiation source 135 and detector 140 to capture radiological images of various areas of interest of the imaged subject 110. Although an exemplary gantry 145 mounted with a C-shaped mobile arm 150 is shown, it should be understood that the type of gantry 145 and mobile arm 145 movably supported thereon can vary.

As shown in FIG. 2, the table 120 generally comprises a tabletop 170 supported by a base 175 from the floor. The tabletop 170 is generally configured to receive the imaged subject 110. The tabletop 170 of the table 120 can be fixed or moveable, and can be interconnected with or independent of the image acquiring system 115. In addition, the table 120 can comprise various conventional advance/withdraw mechanisms, lift mechanisms and/or tilt mechanisms operable to move the tabletop 170 and imaged subject 110 to a desired raised/lowered, tilted, and/or advanced/withdrawn position. It should also be understood that the type of table 120 can vary.

The tool or object 105 can be a surgical tool, navigational tool, a guidewire, a catheter, an endoscopic tool, a laparoscopic tool, ultrasound probe, pointer, aspirator, coil, or the like employed in a medical procedure. Yet, the type of object 105 can vary.

Referring now to FIGS. 1 and 2, the tracking system 125 is generally operable to track or detect a position of the object 105 relative to the acquired image generated by the image acquiring system 115. The exemplary tracking system 125 includes an array or series of tracking elements 180, 185, and 190 connected (e.g., via a hard-wired or wireless connection) to communicate position data to a controller 200 (See FIG. 1). Yet, it should be understood that the number of tracking elements can vary. An embodiment of the tracking elements 180, 185, and 190 comprises one or more transmitters or dynamic references in electromagnetic communication or electromagnetically coupled with one or more receivers. At least one of the tracking elements 180, 185, and 190 transmits a field of electromagnetic energy (e.g., 10-20 kHz) operable to be detected by at least one or both or the other tracking elements 180, 185, and 190. In response to passing through a field of electromagnetic energy, the receiver generates a signal indicative of a special relation to the transmitter. Yet, it should be understood that the type of mode of coupling, link or communication (e.g., rf, infrared light, etc.) operable to measure a spatial relation can vary.

Still referring to FIGS. 1 and 2, in the exemplary embodiment of the system 100, the tracking element 180 is attached at the object 105 being tracked traveling through the imaged subject 110. The tracking element 180 can be detachably connected to the object 105 via a snap-on assembly, a slide-in hole, or include some other mechanical connector assembly known in the art. The tracking element 185 is attached at the imaged subject 110 and moves with the imaged subject 110. An embodiment of the tracking element 185 can be attached at a headset mounted on the imaged subject 110. Yet, the attachment location of the tracking element 185 at the imaged subject 110 can vary. The tracking element 190 is detachably connected at and moves with the tabletop 170 of the table 120. One embodiment of the tracking element 190 includes a transmitter having a plurality of coils (e.g., Hemholtz coils) operable to generate an electromagnetic gradient field in the region of interest on the table 120 where tracking is to occur. Another embodiment of the tracking element 190 is a receiver that comprises at least one conductive loop operable to generate an electric signal indicative of a position relative to an electromagnetic field generated by one or more of the other tracking elements 180 and 185 in the predetermined work space or region of the table 120 where tracking is to occur.

Referring back to FIG. 1, the controller 200 is generally connected in communication with each of the tracking elements 180, 185, and 190, a user interface 210, and a display 215. An embodiment of the controller 200 generally includes a processor 220 in communication with a memory 225. The processor 220 can be arranged independent of or integrated with the memory 225.

The processor 220 is generally operable to execute the program instructions representative of acts described herein and stored in the memory 225. The processor 220 can also be capable of receiving input data or information from the user interface 210 or communicating output data for illustration on the display 215. Examples of the processor 220 can include a central processing unit of a desktop computer, a microprocessor, a microcontroller, or programmable logic controller (PLC), or the like or combination thereof.

An embodiment of the memory 225 generally comprises one or more computer-readable mediums such as a hard disk, a floppy disk, CD, CD-ROM, DVD, compact storage medium, flash memory, random access memory, read-only memory, programmable read-only memory, memory stick, or the like or combination thereof. The memory 225 is operable to store the plurality of program instructions for execution by the processor 220, as well as store data generated by the controller 200 and/or input via the interface 210 to the controller 200.

The user interface 210 can include any input device operable to receive and communicate information data from user to the controller 200. The user interface 210 can include a mouse device, pointer, keyboard, touch screen, or other like device capable of receiving a user directive. The user interface 210 may include capabilities for voice recognition, motion tracking, and/or eye tracking.

The display 215 is generally a device operable to illustrate output data for viewing by the user. The exemplary display 215 is operable to simultaneously illustrate or fuse static or real-time image data generated by the image acquiring system 115 with tracking data generated by the tracking system 125. The display 215 can include a cathode ray monitor, a liquid crystal display (LCD) monitor, a plasma monitor, or the like or combination thereof. The display 215 is capable of illustrating two-dimensional, three-dimensional image and/or four-dimensional image data through shading, coloring, and/or the like.

Having provided a description of the general construction of the system 100, the following is a description of a method 300 (see FIG. 4) of operating of the system 100 in relation to the imaged subject 110. Although an exemplary embodiment of the method 300 is discussed below, it should be understood that one or more acts or steps comprising the method 300 can be omitted or added. It should also be understood that one or more of the acts can be performed simultaneously or at least substantially simultaneously, and the sequence of the acts can vary. Furthermore, it is embodied that at least several of the following acts can be represented as a series of modules of computer-readable program instructions to be stored in the memory 225 of the controller 200 for execution by the processor 220.

Figure 5:
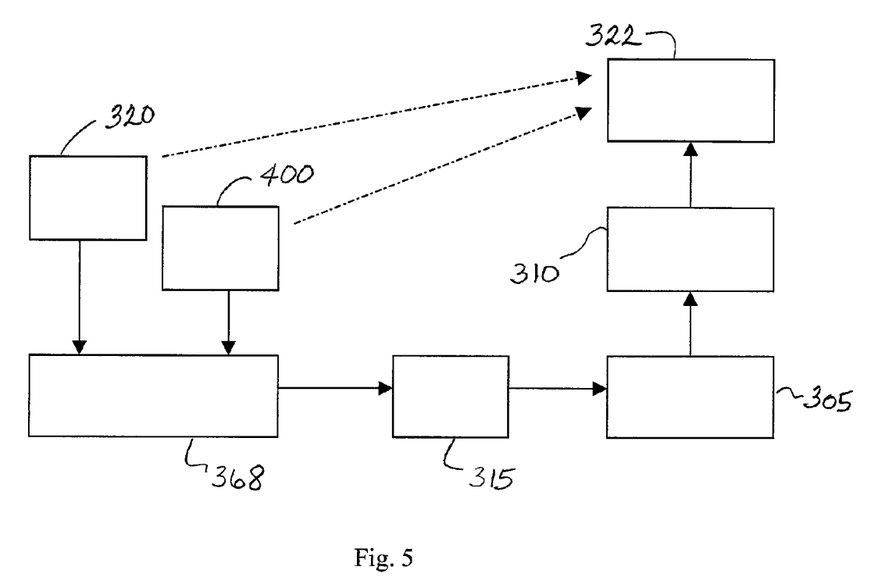
FIG. 5 shows a schematic flow diagram of an embodiment of a method of registering a tracking element of an object for illustration as a virtual image in combination with an acquired image of the subject.

Referring to FIGS. 2 and 5, assume, for sake of example, that a location of the gantry 145 of the image acquiring system 115 is defined with a gantry coordinate system 305, a location of the image detector 140 is defined with a detector coordinate system 310, a location of the table 120 is defined with a table coordinate system 315, a location of the imaged subject 110 is defined with a subject coordinate system 320, and the acquired image by the detector 140 is defined by an image coordinate system 322. Although all of these coordinate systems 305, 310, 315, 320, and 322 are described as Cartesian x-y-z coordinate systems, the type of coordinate systems 305, 310, 315, 320, and 322 (e.g., polar, etc.) can vary. In addition, the exemplary location and orientation of the coordinate systems 305, 310, 315, 320, and 322 can vary.

Figure 4:
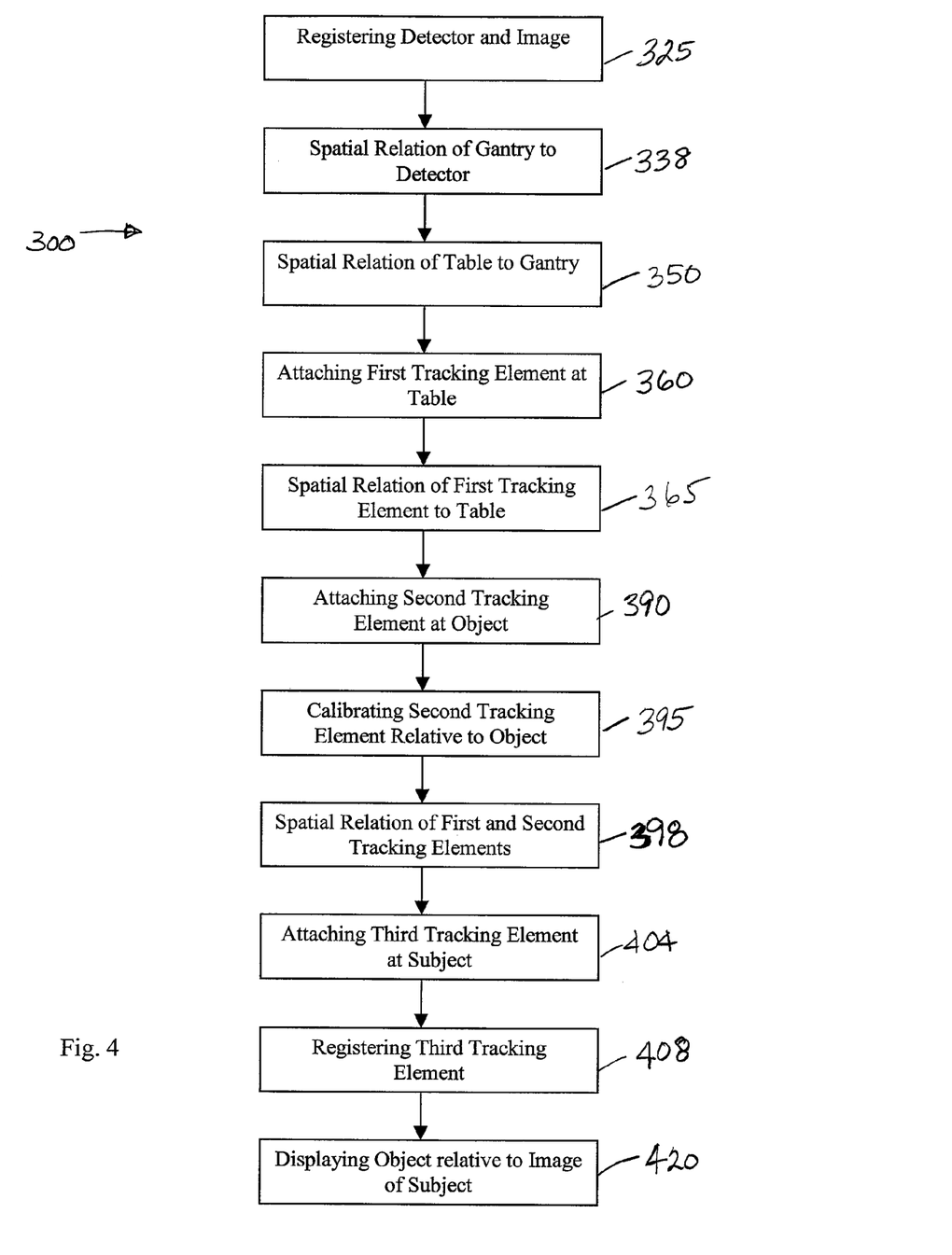
FIG. 4 illustrates a schematic flow diagram of an embodiment of a method of navigating an image-guided object through an area of interest of an imaged subject.

Referring now to FIG. 4, act 325 includes registering the detector coordinate system 310 of the detector 140 with respect to the image coordinate system 322 of the acquired image(s). An embodiment of the act 325 generally includes an offline procedure of acquiring a spatial relation between the image and the detector 140 for communication to the controller 200 before the imaged subject 110 is positioned on the table 120.

Figure 3:
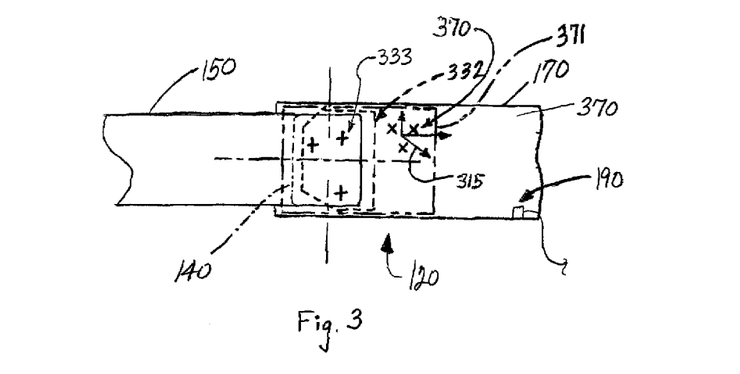
FIG. 3 shows a schematic diagram of an embodiment of an arrangement that includes a phantom having a series of fiducial markers positioned on a table in combination with an image detector mounted on a mobile arm.

As shown in FIG. 3, one embodiment of the act 325 includes acquiring image data of a phantom 332 placed on the table 120, in place of the imaged subject 110. An embodiment of the phantom 332 comprises of a series of fiducial markers 333 located at a predetermined spatial relationship and orientation with respect to one another. The shape (e.g., cylinder, etc.) and dimensions of the phantom 332 and the fiducial markers 333 can vary. The act 325 of registering includes aligning acquired image data of the phantom 332, as generated by the image acquiring system 115, with the actual physical dimensions and orientation of the phantom 332. The manufacturer may provide predetermined measurements of the parameters that define the spatial relation and orientation of the fiducial markers 333 of the phantom 332. Alternatively, the spatial relation and orientation of the fiducial markers 333 can be measured optically in accordance to conventional techniques associated with using a dual camera system 335. The predetermined spatial relationship can be communicated directly or indirectly and stored at the controller 200 of the tracking system 125.

The controller 200 is operable to correlate or match a calculated physical spatial relation and orientation of the fiducial markers 333 of the phantom 332 with the location of the fiducial markers 333 illustrated in the acquired image data using conventional algorithms so as to register with the detector coordinate system 310 of the image detector 140 and the image coordinate system 322 of the image acquired by the image detector 140.

Referring now to FIGS. 2 and 4, act 338 includes acquiring a spatial relation of the coordinate system 305 of the gantry 145 relative to the coordinate system 310 of the image detector 140. As shown in FIG. 2, the tracking system 125 can receive and store measured intrinsic parameters of the image detector 140 in spatial relation to the gantry 145. Examples of the intrinsic parameters can include mechanically measuring an effective focal length (i.e., the exact distance from the radiation source 135 to the image plane) and a location of a focal spot 339 (i.e., location where the optical axis pierces the image plane) for various positions of the mobile arm 150 in spatial relation to the predetermined location of the gantry coordinate system 305 of the gantry 145. The gantry 145 includes at least one encoder 340 associated with motors that drive movement of the image detector 140 in relation to the gantry coordinate system 305 and the table 120. The image acquiring system 115 is operable to translate signals from the encoder 340 using conventional algorithms and predetermined intrinsic parameters descriptive of the gantry 145 in relation to the image detector 140 so as to automatically calculate a spatial relation of the coordinate system 310 of the image detector 140 in relation to the gantry coordinate system 305 of the gantry 145.

Referring back to FIGS. 2 and 4, act 350 includes acquiring a spatial relation between the gantry coordinate system 305 and the table coordinate system 315 as defined by the table 120. The spatial relation can be mechanically measured prior to acquiring images of the imaged subject 110 and communicated to the memory 225 of controller 200 (See FIG. 1).

Still referring to FIGS. 2 and 4, act 360 includes attaching the tracking element 190. In accordance with one embodiment, the tracking element 190 is attached at the table 120. Yet, the tracking element 190 is not located in a field of view of acquired images captured by the image detector 140. However, the tracking element 190 can be attached anywhere on the table 120, including, but not limited to, the tabletop 170 and the base 175. Although the tracking element 190 is described attached at the table 120, the tracking element 190 can otherwise be selectively attached or connected anywhere other than the table 120 (e.g., embedded in the floor as illustrated in dashed line and by reference 362, at the gantry 145, etc.) and yet in fixed relation to the table 120. Thus, the location of attachment of the tracking element 190 can vary.

Act 365 includes acquiring a spatial relation of the tracking element 190 and a tracking coordinate system 368 as defined by the tracking element 190, relative to the table coordinate system 315 of the table 120. Act 365 also includes registering the spatial relation of the tracking coordinate system 368, as defined by the location of the tracking element 190, relative to the coordinate system 310 of the detector 140 and the image coordinate system 322 of the of the image acquired by the detector 140. Act 365 can be performed offline, before the imaged subject 110 is placed on the table 120, by translating the above-described acquired spatial relations between the image coordinate system 322 and the detector coordinate system 310, the spatial relation between the detector coordinate system 310 and the gantry coordinate system 305, the measured spatial relation between the gantry coordinate system 305 and the table coordinate system 315, and the acquired spatial relation between the tracking coordinate system 368 (as defined by tracking element 190) relative to the table coordinate system 315.

Referring now to FIG. 3, one embodiment of act 365 includes temporarily pointing or locating one of the other tracking elements 180 and 185 or additional similar tracking elements at one or more fiducial markers 370 that define the coordinate system 315 of the table 120. Assume the location of the fiducial markers 370 in relation to the dimensions and orientation of the table 120 can be predetermined offline either via a mechanical, electromagnetic or optical measurement. Also assume that the location or spatial relation of the fiducial markers 370 relative to the fiducial markers 333 of the phantom 332 can be known or predetermined offline via act 325. Thus, act 325 can be performed simultaneously with act 365. Having registered the detector coordinate system 310 of the image detector 140 with respect to the image coordinate system 322, the controller 200 can use the acquired image data including the location the fiducial markers 333 of the phantom 332 in spatial relation to the location of the fiducial markers 370 of the table 120 so as to automatically register the spatial relation of the fiducial markers 370 relative to the coordinate system 310 of the image detector 140 and the image coordinate system 322.

An embodiment of the tracking element 190 is fixed at the tabletop 190 of the table 120 independent of and at a spaced distance from the fiducial markers 370, such that the tracking element 190 is not part of any portion of, and is not enclosing or surrounding any portion of, any of the fiducial markers 333 and 370. The tracking elements 180, 185 and 190 are in electromagnetic communication with one another so as to generate a signal indicative of a measured spatial relation of the tracking element 190 relative to the fiducial markers 370 for communication to the tracking system 125. Knowing the spatial relation of the tracking element 190 relative to the fiducial markers 370 fixed at the table 120, the controller 200 can automatically register the location of the tracking coordinate system 368 as defined by the tracking element 190, via the acquired spatial relation between the gantry coordinate system 305 relative to the table coordinate system 315, relative to the detector coordinate system 310 of the image detector 140 and the image coordinate system 322 of the image.

Still referring to FIG. 3, another embodiment of act 365 includes measuring the spatial relation of the tracking element 190 relative to the image detector 140. This embodiment of act 365 includes measuring a spatial relation of the tracking element 190 relative to other tracking elements 180 and 185 or additional similar tracking elements temporarily pointed or located at the fiducial markers 333 of the phantom 332. Having already measured the spatial relation of the fiducial markers 333 of the phantom 332 relative to the image detector 140, and having registered the coordinate system 310 of the image detector 140 with the image coordinate system 322 as defined by the image as described above, and knowing the spatial relation of the tracking element 190 relative to the fiducial markers 333 of the phantom 332, the controller 200 can automatically register the location of the tracking coordinate system 368 as defined by the tracking element 190 relative to the detector coordinate system 310 of the image detector 140 and the image coordinate system 322.

In yet another embodiment of act 365, the fiducial markers or landmarks 370 of the table 120 can be integrated to include the tracking element 190 or additional tracking elements 372 and 374 in a manner that allows the controller 200 to predetermine, in an offline manner, the spatial relation of the table coordinate system 315 of the table 120 relative to the image coordinate system 322.

Referring back to FIGS. 2 and 4, act 390 includes attaching the tracking element 180 at the object 105 to be moved through the imaged subject 110. The tracking element 180 can be integral with the object 105, or attached with a mechanical connector (e.g., snap-on, inserted through an opening, etc.) to the object 105. The tracking element 180 is linked in electromagnetic communication with the tracking element 190 at the table 120 so as to generate a signal representative of a location or movement of the tracking element 180 relative to the other tracking elements 190 and respective coordinate system 355 for communication via a wireless or wired connection to the controller 200. It should be understood that the object 105 and attached tracking element 180 can be used to point to the fiducial markers 333 and 370 (See FIG. 3) in act 365.

Act 395 includes calibrating a measured distance between the tracking element 180 and a tip or pointer of the object 105 to be tracked. Act 398 includes acquiring the spatial relation between the tracking element 190 at the table 120 and the tracking element 180 attached at the object 105. The act 398 can be performed continuously or on a predetermined periodic basis. An embodiment of act 398 can further include registering a coordinate system 400 as defined by a location of the object or tool 105 with the image coordinate system 322. At least one of the tracking elements 180 and 190 generates the signal representative of data indicative of a measured spatial relation of the tracking element 180 at the object 105 relative to the other tracking element 190 and associated coordinate system 368 to the controller 200. Based on the signals from one or both of the tracking elements 180 and 190, the controller 200 automatically continuously or periodically updates this measured spatial relation to track movement of the tracking element 180 at the object 105 and the tracking element 190 at the table 120 relative to the image coordinate system 322 of the acquired image by the image detector 140, and the gantry coordinate system 305.

As illustrated in FIG. 5, the above-description discusses how the controller 200 of the tracking system 125 acquires the location of the object coordinate system 320 as defined by the object 105 in spatial relation to the tracking coordinate system 368 as defined by the tracking element 190, in spatial relation to the table coordinate system 315 as defined by the table 120, in spatial relation to the gantry coordinate system 305 as defined by the gantry 145, in spatial relation relative to the image coordinate system 322 of the image and the detector coordinate system 310 of the image detector 140.

Although not necessary, the embodiment of the method 300 can further comprise the act 404 of attaching and fixing the tracking element 185 to the imaged subject 110 positioned on the table 120 ready for image acquisition by the image detector 140 of the system 115. For example, the tracking element 185 can be attached at a region of interest (e.g., sinus area, spinal area) of the imaged subject 110, or be part of a headset mounted on the cranium of the imaged subject 110. The location of the tracking element 185 at the imaged subject 110 can vary. The tracking element 185 is connected in communication with the controller 200, and is in electromagnetic communication with the tracking elements 180 and 190. The tracking element 185 defines a subject coordinate system 406. Thereby, the tracking element 185 defines a dynamic reference point with respect to the image subject 110.

Referring back to FIGS. 2 and 4, act 408 includes registering the subject coordinate system 406 of the imaged subject 110 with the image coordinate system 322. Having attached the tracking element 190 at the table 120 and having attached the tracking element 180 at the object 105, the controller 200 is capable of automatically measuring the spatial relation of the tracking element 180 relative to both tracking elements 185 of the object 105 and the tracking element 190 of the table 120. As shown in FIG. 5, the above-description how the controller 200 of the system 125 acquires the location of the imaged subject 110 in spatial relation to the to the tracking coordinate system 368 as defined by the tracking element 190, in spatial relation to the table coordinate system 315 as defined by the table 120, in spatial relation to the gantry coordinate system 305 as defined by the gantry 145, in spatial relation relative to the image coordinate system 322 of the image and the detector coordinate system 310 of the image detector 140.

Act 420 includes displaying the tracked location of the object 105 in spatial relation to an anatomical roadmap 425 of the imaged subject 110 for illustration to and viewing by the physician or clinician performing a medical procedure. The acquired image data of the imaged subject 110 generated by the image acquiring system 115 is included to build the anatomical roadmap 425 for illustration on the display 215. It should be understood that the anatomical roadmap 425 can include various types of diagnostic or interventional images or fusion of images acquired by various image acquiring systems 115. As the object 105 travels with the imaged subject 110, the controller 200 tracks movement of the object 105 in spatial relation relative to the anatomical roadmap 425 for illustration on the display 215, such as in a surgical suite or operating room. The act 420 includes generating a composite image that comprises a graphic virtual image 430 of the object 105 in spatial relation to the anatomical roadmap 425, including the image of the imaged subject 110 as acquired by the detector 140,for illustration on the display 215. Various types of graphics, such as a cursor, triangle, square, cross-hairs, etc. can be used to illustrate the graphic virtual image 430. With the ability to track movement of the object 105, the physician can more safely perform delicate procedures without damaging critical surrounding structures such as arteries and nerves that years ago would have been considered impossible.

The controller 200 is operable to track movement of the object 105 relative to the anatomical roadmap 425 in accordance to known mathematical algorithms programmed as program instructions of a software for execution by the processor 220 of the controller 200. An exemplary navigation software is INSTATRAK® as manufactured by the GENERAL ELECTRIC® Corporation. The exemplary software is operable to use two- or three-dimensional MRI, CT and/or X-ray acquired image data generated by the image acquiring system 115 to build a digitized model of a patient's anatomy, and electromagnetic (EM) tracking technology that operates as a type of "global positioning system" to show the location of the object 105 in real-time. The virtual image 430 of the object 105 in spatial relation to the anatomical roadmap 425 can appear on one or more displays 215 to guide the physician during delicate procedures such as Ear, Nose and Throat (ENT), Neurocranial or Spinal surgical procedures.

In one example, the image acquiring system 115 includes a CT imaging system 435 operable to acquire a CT image scan and an endoscopic imaging system 440 operable to acquire an endoscopic image scan, respectively, and illustrated simultaneously or fused together for illustration on the display 215 while the surgeon moves the object 105 through the imaged subject 110. The tracking system 125 generates the virtual image 430 (e.g., cross-hairs) of the object 105 for visualization on the anatomical roadmap 425 that includes both the CT image scan and the endoscopic image scan. The system 100 may be used in guiding various objects 105, such as shunts and catheters, or in performing biopsies. The system 100 may also be employed by neurosurgeons in performing cranial surgeries so as to reduce risk to motor, speech, and somatosensory areas.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system for navigating an image-guided object traveling in an area of interest of an imaged subject supported on a table in relation to an acquired image of the imaged subject, comprising:
    an image detector operable to generate the acquired image of the imaged subject, a location of the image detector defining a detector coordinate system;
    a gantry in mobile support of the image detector relative to the table, a location of the gantry defining a gantry coordinate system;
    a first tracking element fixed with respect to the table in support of the imaged subject, the first tracking element defining a first tracking coordinate system, the first tracking element not located within a field of view of the image detector; and
    a second tracking element attached at the object traveling through the imaged subject, the second tracking element in electromagnetic communication with the first tracking element, the second tracking element defining a second tracking coordinate system;
    a controller electrically connected in communication with the first and second tracking elements, the controller having a processor operable to execute a plurality of program instructions stored in a memory, the plurality of program instructions comprising:
    registering the image coordinate system with the detector coordinate system;
    acquiring a spatial relation between the detector coordinate system and the gantry coordinate system;
    acquiring a spatial relation between the gantry coordinate system and a table coordinate system;
    registering the first tracking coordinate system defined by the first tracking element with respect to the table coordinate system;
    acquiring the spatial relation between the first tracking element relative to the second tracking element;
    translating the spatial relation between first tracking element and the second tracking element at the object automatically into a spatial relation of the object relative to the image; and
    generating a composite image comprising a virtual image of the object in spatial relation to the image of the imaged subject acquired by the image detector.

2. The system of claim 1, wherein the controller automatically registers a location of the image coordinate system in spatial relation to the first and second tracking coordinate systems.

3. The system of claim 1, wherein the first tracking element is attached at the table.

4. The system of claim 1, further comprising a third tracking element attached at the imaged subject and in electromagnetic communication with at least one of the first and second tracking elements, the third tracking element defining a third tracking coordinate system and is a dynamic reference with respect to the imaged subject, wherein the controller automatically translates a spatial relation between the third tracking element and the second tracking element at the object automatically into a spatial relation of the object relative to the imaged subject.

5. The system of claim 1, wherein the act of registering the first tracking coordinate system with respect to the image coordinate system includes:
    acquiring an registration image with the image detector of a phantom having at least three fiducial markers positioned on the table in place of the imaged subject having been removed; and
    measuring a spatial relation via an electromagnetic link between the first tracking element attached at the table and the second tracking element of the object located at one of the at least three fiducial markers of the phantom.

6. The system of claim 1, wherein the act of registering the first tracking coordinate system with respect to the image coordinate system includes:
    measuring a spatial relation via an electromagnetic link between the first tracking element attached at the table and the second tracking element at the object located at one of at least three fiducial markers fixed at the table, the at least three fiducial markers having a predetermined measured spatial relation relative to the gantry coordinate system and located at a spaced distance from the first tracking element.

7. The system of claim 1, wherein first tracking element is connected at the floor.

8. The system of claim 1, wherein the first tracking element is operable to be attached at any location on the table.

9. A method of navigating an image-guided object through an area of interest of an imaged subject, the method comprising the acts of:
    acquiring an image of the imaged subject with an image detector;
    acquiring a spatial relation between a detector coordinate system defined by a location of the image detector and a gantry coordinate system defined by a location of a gantry in mobile support of the image detector;
    acquiring a spatial relation between the gantry coordinate system and a table coordinate system defined by a location of a table;
    registering the table coordinate system with respect to a first tracking element fixed with respect to the table, the first tracking element defining a first tracking coordinate system;
    acquiring a spatial relation between the first tracking element relative to a second tracking element attached at the object;
    translating the spatial relation between first tracking element relative to the second tracking element at the object automatically into a spatial relation of the object relative to the image coordinate system; and generating a composite image comprising a virtual image of the object in spatial relation to the image of the imaged subject.

10. The method of claim 9, wherein the table coordinate system of the table is defined by at least three fiducial markers fixed at the table, and wherein the act of acquiring the spatial relation between the first tracking element and the table coordinate system includes measuring a spatial relation between the first tracking element and a third tracking element located at one of the at least three fiducial markers on the table.

11. The method of claim 9, wherein the first tracking element is not located in the field of view of the image acquired by the image detector, and wherein the first tracking element is spaced a distance from the at least three fiducial markers on the table such that the first tracking element is not part of, and is not partially surrounding the at least three fiducial markers on the table.

12. The method of claim 9, the method further comprising the act of:

attaching a third tracking element at the imaged subject, the third tracking element in communication with at least one of the first and second tracking elements, the third tracking element defining a dynamic reference of the imaged subject; and automatically translating a spatial relation between the third tracking element and the second tracking element at the object and the first tracking element at the table automatically into a spatial relation of the object relative to the image of the imaged subject.

13. The method of claim 9, wherein the first tracking element is operable to be selectively attached at any location on the table.

14. The method of claim 9, wherein the act of registering the table coordinate system relative to the first tracking element includes measuring the spatial relation of the first tracking element relative to the second tracking element at the object that is pointed at one of the least three fiducial markers of a phantom of known dimension placed on the table in replacement of the imaged subject and within in a field of view of the image detector, the first tracking element not located in the field of view of the image acquired by the image detector.

15. The method of claim 9, wherein the act of registering the table coordinate system relative to the first tracking element includes acquiring a calibration image of a fiducial marker of a phantom positioned on the table, and measuring a spatial relation via an electromagnetic link between the first tracking element attached at the table and the second tracking element temporarily located at the fiducial marker of the phantom, the first tracking element not located within a field of view of the calibration image.

16. The method of claim 9, the method further comprising the act of automatically registering the gantry coordinate system of the gantry with respect to both the first and second tracking coordinate systems.

17. A system for navigating an image-guided object traveling in an area of interest of an imaged subject supported on a table, comprising:

an image detector operable to acquire an image of the imaged subject;

a gantry in mobile support of the image detector in relation to the table;

a first tracking element attached at the table, the first tracking element defining a first tracking coordinate system, the first tracking element not located within a field of view of the image;

a second tracking element attached at the image-guided object traveling through the imaged subject, the second tracking element in electromagnetic communication with the first tracking element;

a third tracking element attached to the imaged subject and in electromagnetic communication with at least one of the first and second tracking elements, the third tracking element defining a third tracking coordinate system; and a controller electrically connected in communication with the image detector and the first, second, and third tracking elements, the controller having a processor in communication with a memory, the processor operable to execute a plurality of program instructions stored in the memory, the plurality of program instructions comprising the acts of:

registering an image coordinate system of the image of the imaged subject with a detector coordinate system defined by a location of the image detector;

acquiring a spatial relation between the detector coordinate system and a gantry coordinate system defined by a location of the gantry;

acquiring a spatial relation between the gantry coordinate system and a table coordinate system defined by the table;

registering the first tracking coordinate system as defined by a first tracking element with respect to the table coordinate system;

acquiring the spatial relation between the first tracking element and a second tracking element attached at the object navigated through the image subject;

translating the spatial relation between first tracking element at the table and the second tracking element at the object automatically into a spatial relation of the object relative to the image of the imaged subject; and generating a composite image comprising a virtual image of the object in spatial relation to the image of the imaged subject acquired by the image detector.

18. The system of claim 17, wherein the first tracking element is not located in the field of view of the image of the imaged subject as acquired by the image detector.

19. The system of claim 17, wherein the act of registering the first tracking coordinate system with respect to the image coordinate system includes:

acquiring an image via the image detector of a phantom having at least three fiducial markers positioned on the table in place of the imaged subject; and measuring a spatial relation via an electromagnetic link between the first tracking element attached at the table and the second tracking element of the object located at one of the at least three fiducial markers of the phantom.

20. The system of claim 17, wherein the act of registering the first tracking coordinate system with respect to image coordinate system includes:

measuring a spatial relation via an electromagnetic link between the first tracking element attached at the table and the second tracking element at the object located at one of at least three fiducial markers fixed at the table, the at least three fiducial markers having a predetermined measured spatial relation to the gantry coordinate system and located at a spaced distance from the first tracking element.

* * * * *